United States Patent [19]

Besozzi

[11] 4,132,741

[45] Jan. 2, 1979

[54] PROCESS FOR PRODUCING HALOPRENE

[75] Inventor: Alfio J. Besozzi, Houston, Tex.

[73] Assignee: Denka Chemical Corporation, Houston, Tex.

[21] Appl. No.: 499,187

[22] Filed: Aug. 21, 1974

Related U.S. Application Data

[60] Division of Ser. No. 149,857, Jun. 3, 1971, abandoned, which is a continuation-in-part of Ser. No. 741,225, Jun. 28, 1968, abandoned, which is a continuation-in-part of Ser. No. 494,899, Oct. 4, 1965, abandoned.

[51] Int. Cl.$^2$ ............................................. C07C 21/20
[52] U.S. Cl. .................................................... 260/655
[58] Field of Search ........................... 260/655, 654 D

[56] References Cited

U.S. PATENT DOCUMENTS 3,028,439   4/1962   Theiling et al. ................. 260/654 D

FOREIGN PATENT DOCUMENTS 6414817   6/1965   Netherlands ............................. 260/655
1055064   1/1967   United Kingdom ..................... 260/655

OTHER PUBLICATIONS

Handbook of Material Trade Names, Zimmerman and Lavene, p. 183, (1953).

*Primary Examiner*—Delbert E. Gantz
*Assistant Examiner*—Joseph A. Boska
*Attorney, Agent, or Firm*—Kenneth H. Johnson

[57] ABSTRACT

Process for producing halogenated butadienes by the dehydrohalogenation of a dihalobutene in the presence of caustic and an anionic surface active agent.

3 Claims, No Drawings

PROCESS FOR PRODUCING HALOPRENE

RELATION TO OTHER APPLICATIONS

This application is a division of Ser. No. 149,857, filed June 3, 1971, abandoned, which was a continuation-in-part of application Ser. No. 741,225, filed June 28, 1968, now abandoned which was a continuation-in-part of application Ser. No. 492,899, filed Oct. 4, 1965, now abandoned.

This invention is directed to a process for producing haloprenes and, more specifically, directed to a process for producing chloroprene. In one of its aspects, this invention is directed to a process for producing haloprenes such as 2-chlorobutadiene by dehydrohalogenating 1,2-dichlorobutene-3.

In the past, the production of haloprene has been accomplished by dehydrohalogenating 1,2-dihalobutene-3 in the presence of an alkali material. Carothers, for example, in U.S. Pat. No. 2,038,538 discloses the dehydrohalogenation of 1,2-dichlorobutene-3 to chloroprene with solid sodium hydroxide. Hearne et al in U.S. Pat. No. 2,430,016 report that improved yields of chloroprene are possible when an aqueous alkali solution, rather than a solid alkali metal, is used during the dehydrohalogenation step. A still more recent patent, U.S. Pat. No. 3,079,446, to MacFarlane suggests dehydrohalogenating 1,2-dichlorobutene-3 to chloroprene with an alkali solution in which the alkali metal is dissolved in a mixture of water and a water miscible solvent. Netherlands patent publication 6414817 published June 24, 1965, teaches dehydrohalogenation processes.

Although each of the above mentioned techniques provides a novel means for obtaining chloroprene from 1,2-dichlorobutene-3, the need still exists for a method which will dehydrohalogenate 1,2-dichlorobutene-3 to chloroprene at rates as well as yields which are commercially attractive.

One of the objects of this invention, therefore, is to provide an improved process for producing halobutadienes. Another object of this invention is to provide an economic and efficient method for converting 1,2-halobutene-3 to 2-halobutadiene. A special object is to provide an essentially quantitative method for dehydrohalogenating 1,2-dichlorobutene-3 to chloroprene with little or no formation of polymer or other undesirable products. Still another object of this invention is to provide a process whereby the dehydrohalogenation of 1,2-dichlorobutene-3 occurs at a much faster rate. Numerous other objects of this invention will be apparent from the disclosure which follows.

These objects are accomplished by contacting 1,2-dihalobutene-3 with an aqueous caustic solution in the presence of an anionic emulsifier at a temperature above the boiling point temperature of the haloprene product.

In one embodiment of this invention, the 1,2-dihalobutene-3 is introduced into dehydrohalogenating solution comprising an aqueous alkali solution containing an emulsifying agent while maintaining the temperature of the dehydrohalogenation solution above the boiling point of the haloprene product. Dehydrohalogenation temperatures of between 60° C. and 150° C. at atmospheric pressures are generally used. However, temperatures of between 80° C. and 120° C. are preferred. In dehydrohalogenating 1,2-dichlorobutene-3, for example, a temperature of between 90° C. and 95° C. has been found to be most suitable.

Although the dehydrohalogenation reaction is normally conducted at atmospheric pressures, pressures above or below atmospheric may also be used, if desired.

Anionic emulsifying agents capable of producing an oil - water (O/W) emulsion and which is stable at a pH of above 10 may be utilized in the process of this invention. Generally, an anionic surface-active emulsifying agent can be added to the dehydrohalogenation solution. Anionic surface-active emulsifying agents, such as alkali soaps having the general formula, RCOOM, wherein RCOO represents a fatty acid containing from 3 to 25 carbon atoms (represented by R) and M is an alkali metal, such as sodium, potassium, lithium, and the like, can be used. Preferably, though, the sodium or potassium salts of long chain fatty acids derived from naturally occurring fats and oils in which the acids are found as the triglycerides, are used. For example, mixed fatty acids derived from tallow, cocoanut oil, palm oil, etc., are especially useful. Examples of suitable alkali soaps include the sodium and potassium salts of oleic acid, palmitic acid, stearic acid, linoleic acid, and the like.

Soaps of multi-valent metals such as calcium, magnesium, zinc, aluminum, and the like, can also, to some extent, be used alone, although they are more often used in conjunction with other emulsifying agents.

In addition to soaps derived from straight chain fatty acids, an acid derived from other sources such as rosin have been found to be especially useful in the preparation of haloprenes. The rosin or rosin derivative soaps are the preferred emulsifiers. For example, the sodium salts of abietic acid or isomers thereof are especially useful in the dehydrohalogenation of 1,2-dichlorobutene-3 to chloroprene. Rosins modified by hydrogenation, dehydro-or polymerization and soaps prepared from these "modified" rosin acids have provided derivatives of abietic acid which are even still more preferred as emulsifying agents, particularly in the dehydrohalogenation of 1,2-dichlorobutene-3 to chloroprene.

Other anionic type surface-active agents which can be used include the aliphatic and alkyl aromatic sulfonates having the general formula

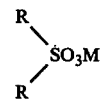

wherein R is an aliphatic radical, aromatic radical, or hydrogen atom and M is an alkali metal. Examples of suitable sulfonate type emulsifying agents include the petroleum sulfonates, such as isopropylnaphthalene sulfonate, sodium heptylbiphenyl sulfonate, sodium salts of polymerized alkyl aryl sulfonic acids, and the like.

A more complete list of useful anionic emulsifying agents can be found in the 1964 publication, Detergents and Emulsifiers, John W. McCutchen, Inc., Morristown, New Jersey, and in Schwartz and Perry, "Surface Active Agents," New York Interscience, Inc., 1949.

It is understood, however, that reference heretofore made to the use of individual emulsifying agents does not prevent their use in combination or mixtures thereof. In many instances, the use of mixtures or combinations tend to enhance the desired activity of the emulsifying agent.

The emulsifying agent is generally present in the dehydrohalogenation solution in amounts of between 0.01 or one percent and 35 percent by weight of the total aqueous solution. Concentrations of between five percent and 15 percent may be used when aqueous caustic solutions are employed for dehydrohalogenating 1,2-dihalobutene-3. Preferred ranges are from about 0.01 to about 15 percent, about 0.09 to about 10 percent and from about 0.2 percent to about 5 percent all based by weight on the total aqueous solution.

The preferred caustic materials which can be used in dehydrogenating 1,2-dihalobutene-3 to haloprene are the alkali metal hydroxides, particularly sodium and potassium hydroxides. However, other alkalies, such as rubidium hydroxide, ammonium hydroxide, lithium hydroxide, lime, or alkaline earth metal hydroxides such as calcium, strontium and barium hydroxides can be employed. The carbonates, such as sodium and potassium carbonate, can also be used, if desired.

The concentration of caustic compound in the aqueous alkali solution may vary considerably and, for the most part, and concentration can be used. However, concentrations of between 5 and 15 percent by weight of caustic compound based on the total weight of the solution are preferred. Generally, enough water should be used to conveniently retain the salt produced in solution and thereby avoid handling troublesome slurried. The volume of solvent and water is normally maintained at a minimum in order to avoid the use of oversized equipment or apparatus. Generally, a continuous fresh supply of caustic solution is added to the reaction system. In dehydrochlorinating 1,2-dichlorobutene-3 to chloroprene, a 10 percent sodium hydroxide solution has been found to be most effective.

Although this invention is operable as a batch dehydrohalogenation process, this invention is readily adaptable to a continuous dehydrohalogenation process whereby a continuous flow of fresh emulsified caustic solution is introduced into the reaction system and whereby the spent emulsified caustic solution is continuously removed. If desired, additional amount of the emulsifying agent separate from the caustic solution may also be added.

The invention is illustrated in the following examples but is not intended to be limited in any manner by such examples.

EXAMPLE 1

456 grams of an aqueous solution containing 10 percent by weight of NaOH (1.14 mols) and a small amount of hydroquinone was added to a one liter 3-neck flask equipped with a stirrer, dropping funnel and distilling arm containing a thermometer, condenser and receiver. A small amount of hydroquinone was also added to the receiver which was maintained at a temperature sufficient to condense the chloroprene produced by packing the receiver in dry ice. The alkali solution was then heated to a temperature of between 90° C. and 95° C. and was maintained at this temperature while 100 grams (0.8 mol) of 1,2-dichlorobutene-3 was gradually added over a period of about an hour. The chloroprene taken overhead was condensed in the receiver, dried over calcium chloride and the refractive index measured. An 88.4 mol percent yield of chloroprene based on the 1,2-dichlorobutene-3 fed was obtained. The chloroprene had a refractive index of 1.4582.

The refractive index of chloroprene is reported by Huntress in "Organic Chlorine Compounds," John Wiley and Sons, 1948, as being $n_D^{20} = 1.4583$.

EXAMPLE 2

The procedure outlined in Example 1 was repeated, with the exception that 45.6 grams of powdered sodium hydroxide was used in place of a 10 percent aqueous solution. The solid sodium hydroxide was heated to a temperature of between 91° C. and 95° C. and the 1,2-dichlorobutene-3 introduced. A chloroprene yield of 67.4 mol percent based on the 1,2-dichlorobutene-3 fed was obtained. The chloroprene had a refractive indix of 1.4605. In this example, the reaction was difficult to control and extensive polymerization was detected.

EXAMPLE 3

Example 1 was repeated with the exception that approximately 50 grams of diethylene glycol was added to the 10 percent aqueous alkali solution. A yield of chloroprene was obtained in this example which was similar to that obtained in Example 1. Attempts to obtain substantially quantitative conversions of the dichloro compound to chloroprene by increasing the reaction temperature resulted in increased polymerization.

EXAMPLE 4

The procedure outlined in Example 1 was repeated again with the exception that 4.5 grams of Dresinate 731* (emulsifying agent) was added to the 10 percent aqueous alkali solution. After the aqueous alkali solution had been emulsified by agitation, the 1,2-dichlorobutene-3 was added over a period of about an hour. A yield of 98.7 percent of chloroprene was obtained. The chloroprene had a refractive index of 1.4583. There was little or no polymerization of the reactants or product detected.

*Dresinate 731 is a registered trade name owned by Hercules Powder Company for an emulsifying agent consisting primarily of sodium dehydroabietate.

EXAMPLE 5

When Example 4 is repeated with 1,2-dibromobutene-3 instead of 1,2-dichlorobutene-3, yields of bromoprene comparable to those in Example 4 are obtained. Runs using mixed halogen feed materials, as well as difluoro and diiodo compounds suggested that other haloprenes can also be obtained by the process of this invention.

One of the unexpected advantages of the invention is the ability to operate at low agitation or stirring rates in the reactor and yet achieve completion of the reaction and separation of the product in less time than conventional processes. This is a significant feature since high speed stirring or agitation equipment represents additional capital cost. Additionally, the increased throughput at low agitation represents a significant advantage since smaller equipment may be designed for the same capacity. The following examples illustrate the improved results obtained according to the invention. In each case, the same reactor and agitator were used.

EXAMPLE 6

As a control, twenty-five grams of 1,2-dichlorobutene-3 were contacted at 90° C. in a reactor with 100 ml. of 10 percent NaOH. The stirring speed of a teflon stirring blade in the reactor was held at about 300 revolutions per minute. The time of complete reaction to and distillation of the chloroprene was approximately 56 minutes.

EXAMPLE 7

The procedure of Example 6 was repeated, except that 1 percent by weight (based on the amount of 1,2-dichlorobutene-3 present) of a sodium alkylnaphthalene sulfonate (known as Dupont Alkanol B) was added. Little or no polymerization was detected.

EXAMPLE 8

The procedure of Example 6 was repeated, except that 1 percent by weight (based on the amount of 1,2-dichlorobutene-3 present) of sodium stearate was added to the reactor. Little or no polymerization was detected, and the time for complete reaction to and distillation of the chloroprene was approximately 18 minutes.

EXAMPLE 9

The procedure of Example 6 was repeated except that 1 percent by weight (based on the amount of 1,2-dichlorobutene-3 present) of Dresinate 731 (sodium dehydroabietate) was added to the reactor. Little or no polymerization was detected, and the time for complete reaction to and distillation of the chloroprene was approximately 14 minutes.

EXAMPLE 10

Example 6 was repeated using a 1 percent addition to the reactor of Tergitol P-28 (sodium di(2-ethylhexyl) phosphate). Little or no polymerization was detected, and the time for complete reaction to and distillation of the chloroprene was 18 minutes.

It is clear from these experiments that significant reductions in reaction time are possible by use of the present invention.

The invention claimed is:

1. A process for dehydrohalogenating 1,2-dihalobutene-3 to haloprene at a high rate of conversion comprising contacting said 1,2-dihalobutene-3 with an aqueous caustic solution of 5 to 15 percent by weight of caustic compound in the presence of from 0.09 to 10 weight percent of an anionic surface active agent of a soap of dehydrogenated rosin maintained at a temperature of between 60° C. and 150° C. for a sufficient time to dehydrohalogenate, and removing therefrom haloprene.

2. A process for dehydrohalogenating 1,2-dihalobutene-3 to haloprene at a high rate of conversion comprising contacting said 1,2-dihalobutene-3 with an aqueous caustic solution of 5 to 15 percent by weight of caustic compound in the presence of from 0.09 to 10 weight percent of the sodium salt of dehydroabietic acid maintained at a temperature of between 60° C. and 150° C. for a sufficient time to dehydrohalogenate, and removing therefrom haloprene.

3. The process according to claim 2 wherein 1,2-dichlorobutene-3 is dehydrohalogenated.

* * * * *

UNITED STATES PATENT OFFICE
CERTIFICATE OF CORRECTION

PATENT NO. : 4,132,741
DATED : January 2, 1979
INVENTOR(S) : Alfio J. Besozzi

It is certified that error appears in the above-identified patent and that said Letters Patent are hereby corrected as shown below:

Column 2, lines 6-7 reads "emulsion and which is stable at a pH of above 10" but should read -- emulsion, which is stable at a pH of above 10, --

Column 2, lines 29 and 30 reads "rosin have been" but should read -- rosin has been --

Column 2, line 36 reads "dehydro- or" but should read -- dehydro-genation or --

Column 3, line 22 reads "and concentration" but should read -- any concentration --

Signed and Sealed this

Twenty-sixth Day of February 1980

[SEAL]

Attest:

SIDNEY A. DIAMOND

*Attesting Officer*     *Commissioner of Patents and Trademarks*